(12) United States Patent
Amanai et al.

(10) Patent No.: US 10,670,836 B2
(45) Date of Patent: Jun. 2, 2020

(54) IMAGE PICKUP APPARATUS

(71) Applicant: OLYMPUS CORPORATION, Hachioji-shi, Tokyo (JP)

(72) Inventors: Takahiro Amanai, Hachioji (JP); Kyoko Iijima, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 44 days.

(21) Appl. No.: 15/847,647

(22) Filed: Dec. 19, 2017

(65) Prior Publication Data

US 2018/0246297 A1    Aug. 30, 2018

(30) Foreign Application Priority Data

Feb. 24, 2017 (JP) .................. 2017-034012

(51) Int. Cl.
| | | |
|---|---|---|
| *G02B 13/00* | (2006.01) | |
| *G02B 9/02* | (2006.01) | |
| *A61B 1/04* | (2006.01) | |
| *A61B 1/00* | (2006.01) | |
| *B60R 11/04* | (2006.01) | |
| *A61B 1/05* | (2006.01) | |
| *A61B 1/07* | (2006.01) | |

(52) U.S. Cl.
CPC ...... *G02B 13/0025* (2013.01); *A61B 1/00096* (2013.01); *A61B 1/00188* (2013.01); *A61B 1/00193* (2013.01); *A61B 1/041* (2013.01); *G02B 9/02* (2013.01); *G02B 13/006* (2013.01); *G02B 13/0035* (2013.01); *A61B 1/00197* (2013.01); *A61B 1/05* (2013.01); *A61B 1/07* (2013.01); *B60R 11/04* (2013.01)

(58) Field of Classification Search
CPC ...... G02B 13/14; G02B 13/00; G02B 13/003; G02B 13/006; G02B 13/0025; G02B 13/18; G02B 3/00; G02B 9/02; G02B 9/60; A61B 1/0096; A61B 1/00188; A61B 1/00193; A61B 1/041; A61B 1/00197; A61B 1/05; A61B 1/07; B60R 11/04
USPC ....... 359/718, 717, 692, 691, 693, 748, 753, 359/793, 795
See application file for complete search history.

(56) References Cited

U.S. PATENT DOCUMENTS

| | | | |
|---|---|---|---|
| 4,467,361 A * | 8/1984 | Ohno ............... | G02B 23/243 250/208.1 |
| 9,104,018 B2 | 8/2015 | Ishihara | |
| 9,417,429 B2 * | 8/2016 | Ishihara ............... | G02B 9/60 |
| 9,453,986 B2 | 9/2016 | Ishihara | |
| 2013/0076900 A1 * | 3/2013 | Mrozek ............... | G02B 13/14 348/144 |

(Continued)

FOREIGN PATENT DOCUMENTS

JP    2013210549 A    10/2013

*Primary Examiner* — Jie Lei
(74) *Attorney, Agent, or Firm* — Holtz, Holtz & Volek PC

(57) ABSTRACT

An image pickup apparatus includes an image forming optical system which includes an aperture stop that determines an axial light beam, and one cemented lens, and an image pickup section which is disposed on an image side of the image forming optical system, and which has a surface which is not flat and is curved to be concave toward the image forming optical system, wherein the cemented lens includes in order from an object side, a first lens having a negative refractive power, a second lens, and a third lens having a positive refractive power.

11 Claims, 13 Drawing Sheets

(56) References Cited

U.S. PATENT DOCUMENTS

2013/0258490 A1\* 10/2013 Ishihara ................ G02B 13/18
359/648
2014/0192254 A1\* 7/2014 Marks .................... G02B 13/06
348/360

\* cited by examiner

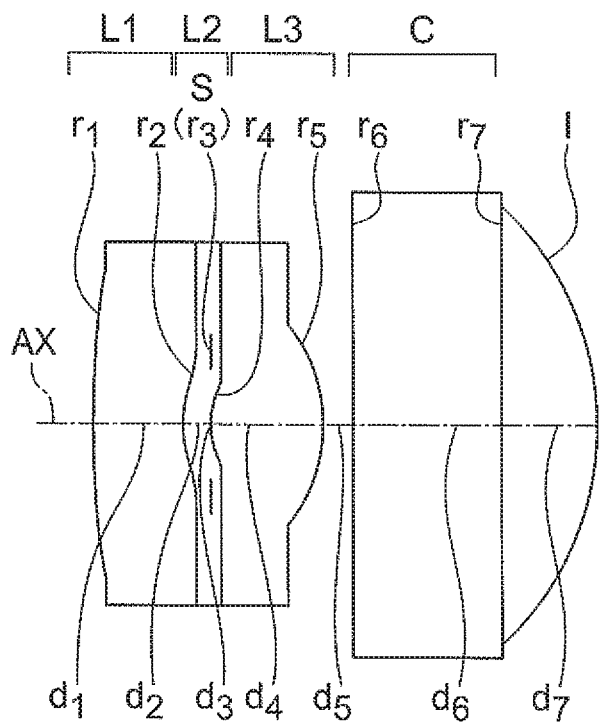
FIG. 2A
FIG. 2B
SA
FNO 2.852
-0.05  0.05
(mm)
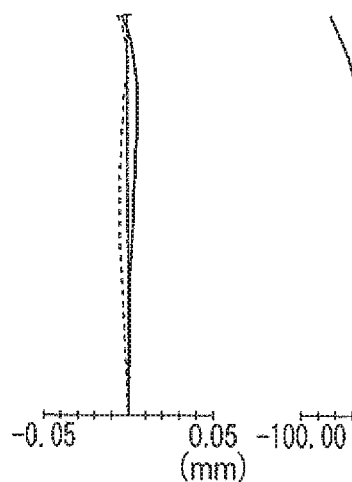
FIG. 2C
AS
FIY 0.73
-0.05  0.05
(mm)
FIG. 2D
DT
FIY 0.73
-100.00  100.00
(%)
FIG. 2E
CC
FIY 0.73
-0.005  0.005
(mm)

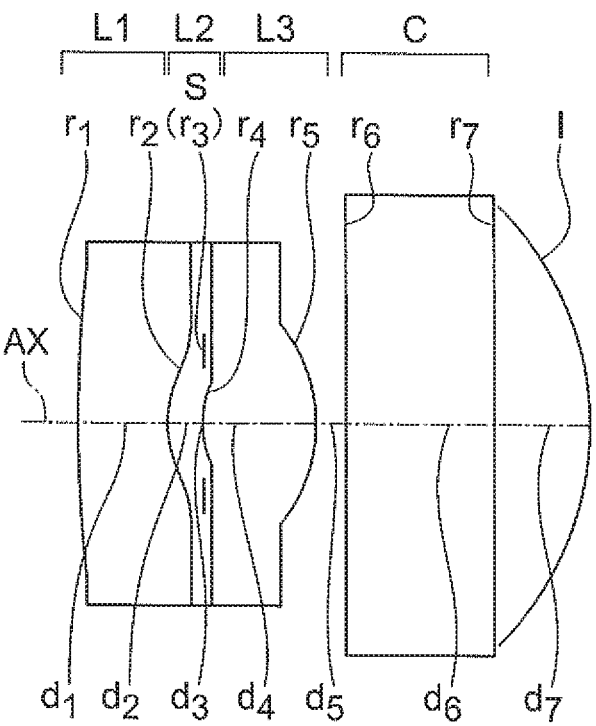
FIG. 4A
FIG. 4B
SA
FNO 2.892
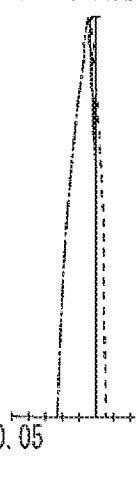
-0.05    0.05
(mm)
FIG. 4C
AS
FIY 0.73
-0.05    0.05
(mm)
FIG. 4D
DT
FIY 0.73
-100.00   100.00
(%)
FIG. 4E
CC
FIY 0.73
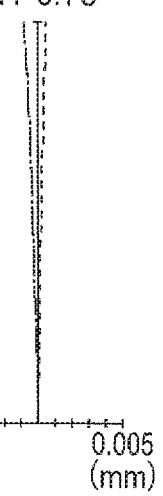
-0.005    0.005
(mm)

SA
FNO 2.889

AS
FIY 0.73

DT
FIY 0.73

CC
FIY 0.73

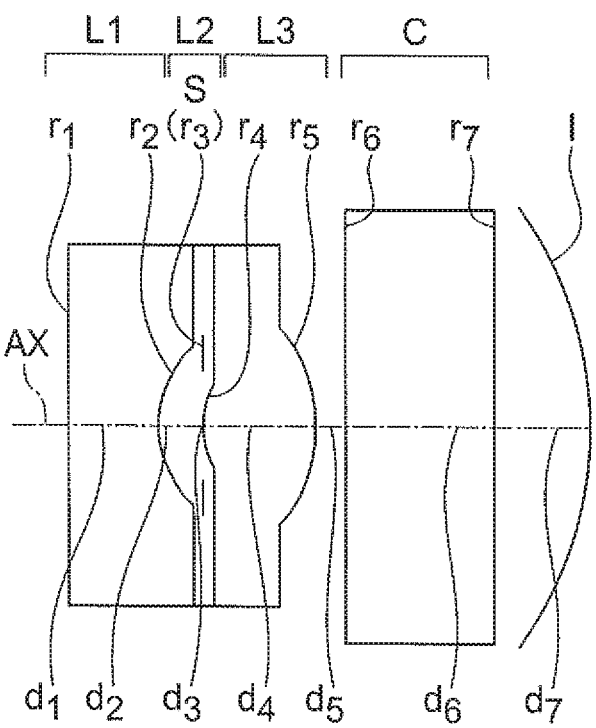
FIG. 6A
FIG. 6B
SA
FNO 3.026
-0.05  0.05
(mm)
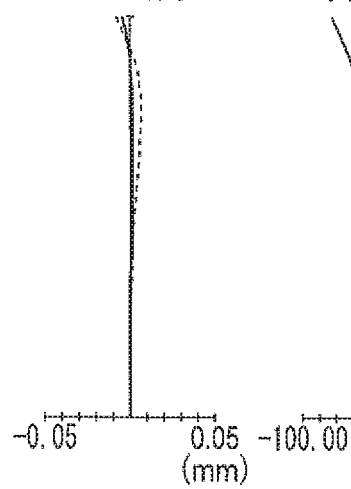
FIG. 6C
AS
FIY 0.73
-0.05  0.05
(mm)
FIG. 6D
DT
FIY 0.73
-100.00  100.00
(%)
FIG. 6E
CC
FIY 0.73
-0.005  0.005
(mm)

SA
FNO 2.947

AS
FIY 0.73

DT
FIY 0.73

CC
FIY 0.73

IMAGE PICKUP APPARATUS

CROSS-REFERENCE TO RELATED APPLICATION

The present application is based upon and claims the benefit of priority from the prior Japanese Patent Application No. 2017-034012 filed on Feb. 24, 2017; the entire contents of which are incorporated herein by reference.

BACKGROUND OF THE INVENTION

Field of the Invention

The present invention relates to an image pickup apparatus.

Description of the Related Art

An optical system which has a wide angle of view, and in which a spherical aberration is corrected favorably and a curved image is formed, has been disclosed in Japanese Patent Application Laid-open Publication No. 2013-210549.

In Japanese Patent Application Laid-open Publication No. 2013-210549, an optical system which includes three lenses and an optical system which includes four lenses have been disclosed. The optical system which includes three lenses includes a positive lens, a positive lens, and a negative lens. The optical system which includes four lenses includes a negative lens, a positive lens, a positive lens, and a negative lens.

SUMMARY OF THE INVENTION

An image pickup apparatus according to at least some of the embodiments of the present invention comprises:

an image forming optical system which includes an aperture stop that determined an axial light beam, and one cemented lens, and an image pickup section which is disposed on an image side of the image forming optical system, and which has a surface that is not flat and is curved to be concave toward the image forming optical system, wherein the cemented lens includes in order from an object side, a first lens having a negative refractive power, a second lens, and a third lens having a positive refractive power.

BRIEF DESCRIPTION OF THE DRAWINGS

FIG. 2A, and FIG. 2B, FIG. 2C, FIG. 2D, and FIG. 2E are a cross-sectional view, and aberration diagrams respectively, of an image forming optical system according to an example 2;

FIG. 4A, and FIG. 4B, FIG. 4C, FIG. 4D, and FIG. 4E are a cross-sectional view, and aberration diagrams respectively, of an image forming optical system according to an example 4;

FIG. 6A, and FIG. 6B, FIG. 6C, FIG. 6D, and FIG. 6E are a cross-sectional view, and aberration diagrams respectively, of an image forming optical system according to an example 6;

DETAILED DESCRIPTION OF THE INVENTION

Figure 1A:
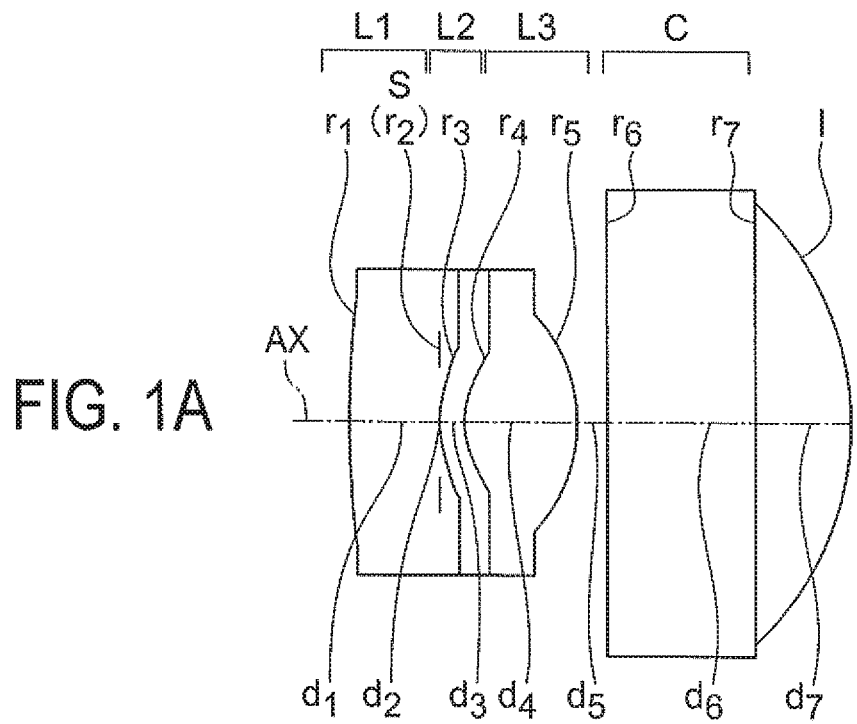
FIG. 1A, and FIG. 1B, FIG. 1C, FIG. 1D, and FIG. 1E are a cross-sectional view, and aberration diagrams respectively, of an image forming optical system according to an example 1.
Figures 1B, 1C, 1D, 1E:
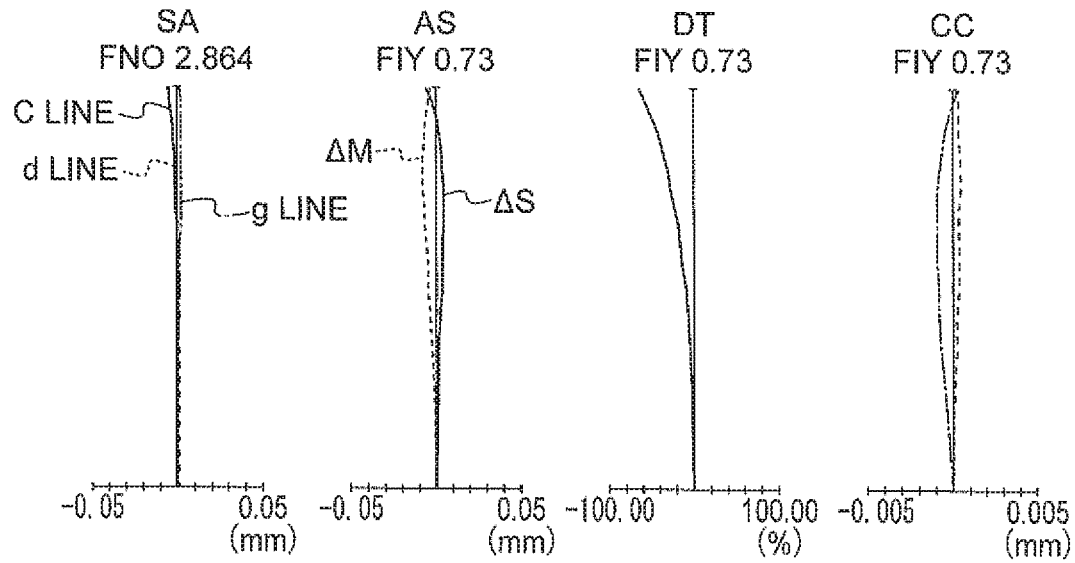
Figure 3A:
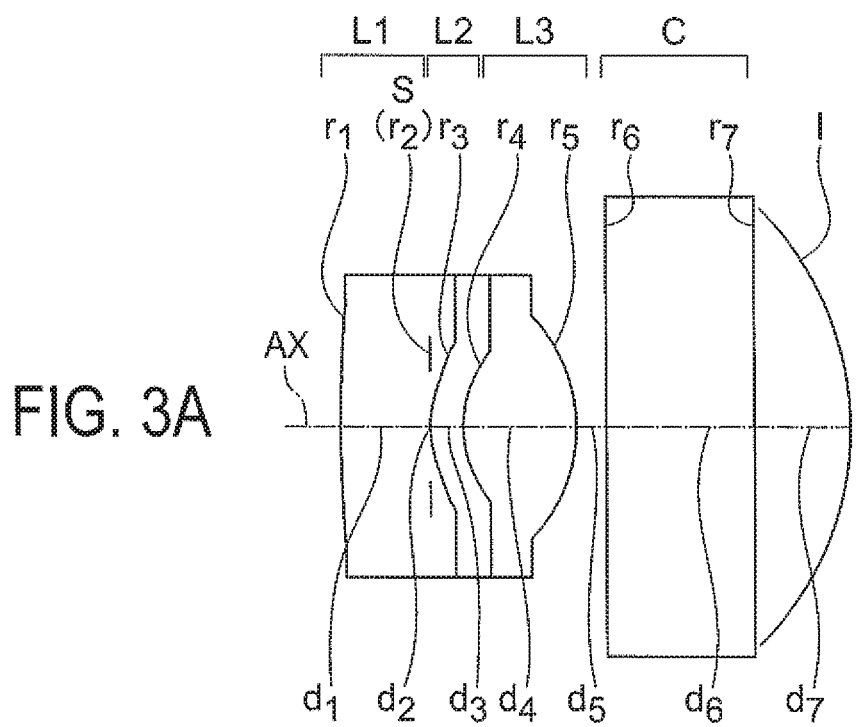
FIG. 3A, and FIG. 3B, FIG. 3C, FIG. 3D, and FIG. 3E are a cross-sectional view, and aberration diagrams respectively, of an image forming optical system according to an example 3.
Figures 3B, 3C, 3D, 3E:
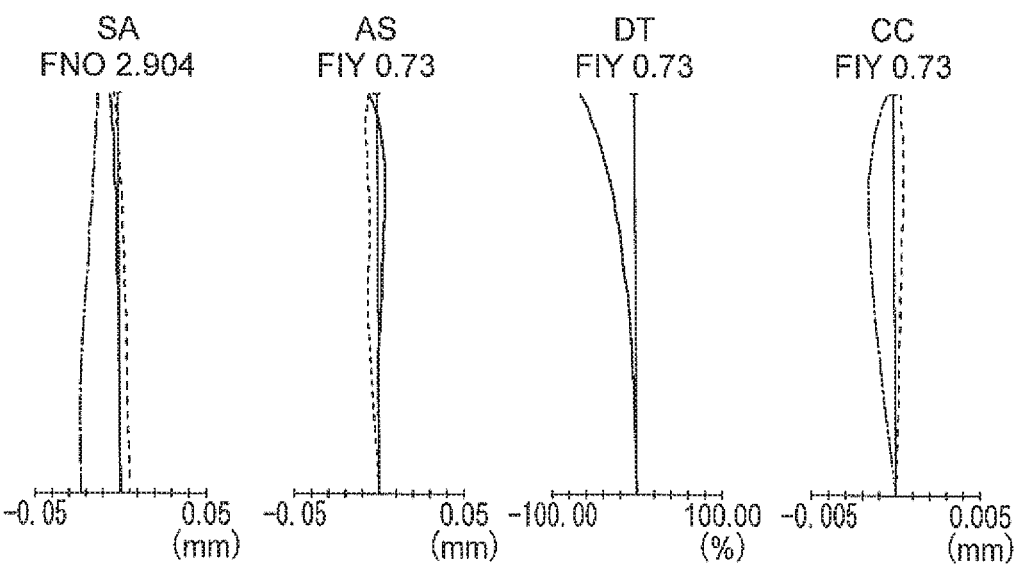
Figure 5A:
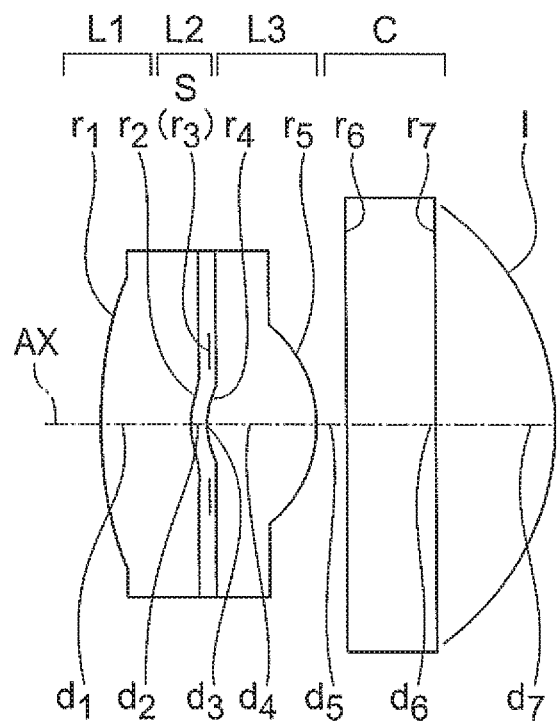
FIG. 5A, and FIG. 5B, FIG. 5C, FIG. 5D, and FIG. 5E are a cross-sectional view, and aberration diagrams respectively, of an image forming optical system according to an example 5.
Figure 5B:
Figure 5C:
Figure 5D:
Figure 5E:
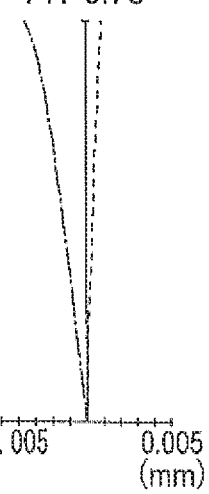
Figures 7A, 7B, 7C, 7D, 7E:
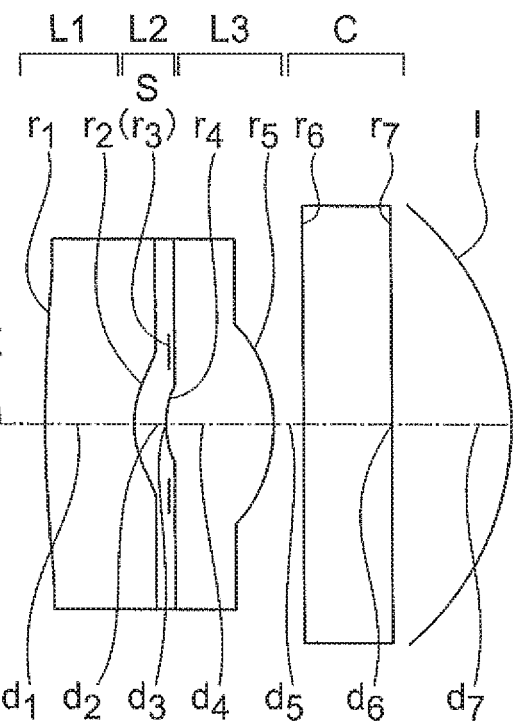
FIG. 7A, and FIG. 7B, FIG. 7C, FIG. 7D, and FIG. 7E are a cross-sectional view, and aberration diagrams respectively, of an image forming optical system according to an example 7.

Prior to describing the examples, an action and an effect of an embodiment according to certain aspects of the present invention will be described below. For describing specifically the action and the effect of the present embodiment, the description will be made by citing concrete examples. Similar to a case of examples to be described later, the aspects to be exemplified are some of the aspects of the present invention, and there exist a large number of variations of these aspects. Therefore, the present invention is not limited to the aspects that are exemplified.

An image pickup apparatus of the present embodiment includes an image forming optical system which includes an aperture stop that determines an axial light beam, and one cemented lens, and an image pickup section which is disposed on an image side of the image forming optical system, and which has a surface that is not flat and is curved to be concave toward the image forming optical system, wherein the cemented lens includes in order from an object side, a first lens having a negative refractive power, a second lens, and a third lens having a positive refractive power.

The image pickup apparatus of the present embodiment includes the image forming optical system which has a long back focus, and is capable of forming a favorable image, while being small-sized. A favorable image refers to an optical image in which an aberration is corrected favorably from a central portion up to a peripheral portion.

In the image pickup apparatus of the present embodiment, the image forming optical system includes the aperture stop and one cemented lens. The aperture stop is a stop which determines the axial light beam.

The image pickup section is disposed on the image side of the image forming optical system. The image pickup section has a light-receiving surface which is not flat and is curved to be concave toward the image forming optical system. Accordingly, an image that is formed on the light-receiving surface is also curved to be concave toward the object side.

In an optical system which forms an image which is completely or partially curved to be concave toward the object side (hereinafter, referred to as 'curved image'), an occurrence of a curvature of field to certain extent is acceptable. Therefore, in the optical system which forms a curved image, a load of aberration correction is reduced as compared to a load in an optical system which forms a flat image.

For instance, in an optical system which forms a curved image, it is possible to reduce a lens for correcting Petzval sum. Consequently, it is possible to make the optical system small in size.

Moreover, in an optical system which forms a flat image, for correcting the curvature of field favorably, it is necessary to dispose a lens for correction at a position away from an aperture stop. However, when the lens for correction is disposed, an outer diameter of the optical system becomes large, and furthermore, the number of lens components increases. Thus, the lens for correction is one of the causes that make the outer diameter of the optical system large.

Whereas, in an optical system that forms a curved image, it is not necessary to dispose the lens for correction. Consequently, in an optical system that forms a curved image, it is possible to make the outer diameter of the optical system small.

Moreover, a relative illumination, or in other words, a ratio of an amount of light in a central area to an amount of light in a peripheral area, is suppressed from being degraded. Moreover, further occurrence of distortion is suppressed.

Furthermore, for receiving an image of an optical system by an image pickup element having a curved image pickup surface, the optical system may not be let to be a telecentric optical system for making a light ray incident on the image pickup surface to be almost perpendicular. Consequently, in an optical system that forms a curved image, a degree of freedom of a design in order to achieve both of downsizing and optical performance, is widened.

The image forming optical system in the image pickup apparatus of the present embodiment is also an optical system which forms a curved image. Consequently, it is possible to reduce the number of lenses and to make the optical system small-sized. Furthermore, since the degree of freedom of a design is widened, it is possible to realize an optical system having a high imaging performance while securing a wide angle of view such as 90 degrees or more.

In the image pickup apparatus of the present embodiment, the image forming optical system includes in order from the object side to the image side, the first lens having a negative refractive power, the second lens, and a third lens having a positive refractive power. The first lens, the second lens, and the third lens form the one cemented lens. By making such arrangement, it is possible to secure a long back focus and a favorable imaging performance, while being small-sized.

The first lens component has a negative refractive power. By making such arrangement, it is possible to secure a favorable imaging performance from a central portion up to a peripheral portion of the photographing range even when the angle of view is 90 degrees or more.

Moreover, since the third lens has a positive refractive power, with the first lens and the third lens, it is possible to make the image forming optical system an optical system of a retro focus type. Consequently, it is possible to secure the back focus of an adequate length. In this case, it is possible to dispose an optical filter or a cover glass between the optical system and the image pickup section.

An endoscope is an example of an instrument having an application of the image pickup apparatus. In an endoscope, sometimes, a lesion part is to be cauterized by irradiating laser light to the lesion part. The laser light is irradiated while observing a color image of the lesion part.

Illumination by white light is carried out for acquiring the color image of the lesion part. Consequently, the white light and the laser light are irradiated to the lesion part. The white light and laser light are reflected from the lesion part. Both the white light and the laser light are incident on the image forming optical system.

A light intensity of the laser light is extremely high as compared to a light intensity of the white light illumination. Therefore, for acquiring the color image, it is necessary to eliminate the laser light in the image forming optical system. When the elimination of the laser light is not adequate, a quality of the color image is degraded.

In the image pickup apparatus of the present embodiment, as mentioned above, the image forming optical system has the back focus of an adequate length. Therefore, it is possible to dispose the optical filter which eliminates the laser light between the image forming optical system and the image pickup section. As a result, it is possible to suppress the degradation of the quality of image.

Moreover, as dirt is adhered to the light-receiving surface of the image pickup section, the quality of image is degraded. It is possible to prevent the dirt from adhering by providing a cover glass to the light-receiving surface. As mentioned above, the image forming optical system has the back focus of adequate length. Therefore, it is possible to dispose the cover glass between the image forming optical system and the image pickup section. As a result, it is possible to prevent the degradation of image due to adhering of dust.

In the image pickup apparatus of the present embodiment, it is preferable that the following conditional expression (1) be satisfied:

$$0.4 < |\Theta out60/60°| < 1.0 \tag{1}$$

where, $\Theta out60$ denotes an angle made by a predetermined principal light ray incident from an image-side surface of the third lens and an optical axis, and here the predetermined principal light ray is a principal light ray for which an angle made with the optical axis is 60° in a space on the object side of the first lens.

By arranging the image forming optical system to satisfy conditional expression (1), it is possible to prevent an apparent stop diameter from becoming narrow with respect to an off-axis light beam even when an angle of view has become wide. Or, it is possible to arrange the image forming optical system such that an aperture diameter does not become narrow with respect to a light beam incident from a peripheral portion of an image pickup range. This signifies that an effect due to a first root of COS $\Theta$ is reduced. Consequently, it is possible to suppress a reduction in an amount of light in the peripheral portion of the image pickup range.

When expression (1) is not satisfied, as the angle of view becomes wider, the apparent stop diameter with respect to the off-axis light beam becomes narrow. Consequently, the reduction in the amount of light in the peripheral portion of the image pickup range becomes large.

It is preferable that the following conditional expression (1') be satisfied instead of conditional expression (1).

$$0.5 < |\Theta out60/60°| < 0.8 \tag{1'}$$

In the image pickup apparatus of the present embodiment, it is preferable that the following conditional expressions (2) and (3) be satisfied:

$$0.7 < |PS \times Rimg| < 1.5 \tag{2, and}$$

$$0.7 < |EXP/Rimg| < 1.5 \tag{3}$$

where,

PS denotes Petzval's sum for the image forming optical system, and

Petzval's sum PS is expressed by the following expression.

$$PS = \sum_{i=1}^{k} \frac{1}{n_i \times f_i}$$

where, i denotes an order of lenses from the object side in the image forming optical system, k denotes the total number of lenses in the image forming optical system, $n_i$ denotes a refractive index of an $i^{th}$ lens for the d-line, $f_i$ denotes a focal length of the $i_{th}$ lens for the d-line, EXP denotes a distance along the optical axis from the light-receiving surface up to a paraxial exit pupil position of the image forming optical system, and is let to have a negative sign when the paraxial exit pupil position is on the object side of the light-receiving surface, Rimg denotes a radius of curvature of a virtual spherical surface which includes a surface apex and a point in which a principal light ray incident at the maximum angle of view on the image forming optical system intersects the light-receiving surface, letting a point of intersection of the optical axis and the light-receiving surface to be the surface apex.

By arranging the image forming optical system to satisfy conditional expression (2), it is possible to cancel a curvature of field that occurs in the image forming optical system by a curvature of the light-receiving surface. Consequently, it is possible to suppress an effect of the curvature of field on degradation of image.

As a result, even with one cemented lens, it is possible to realize an image forming optical system in which an aberration is corrected adequately. Moreover, it is possible to realize an image pickup apparatus which is capable of acquiring a high-quality image, while being small-sized.

When conditional expression (2) is not satisfied, it is not possible to cancel the curvature of field that occurs in the image forming optical system by the curvature of the light-receiving surface. Consequently, an effect of the curvature of field on the degradation of image becomes large.

In this case, it becomes difficult to form a favorable image with one lens unit. Consequently, there is a degradation of the quality of image acquired.

By arranging the light-receiving surface to satisfy conditional expression (3), a principal light ray corresponding to each image height is incident substantially perpendicularly with respect to the light-receiving surface. This signifies that an effect due to the first root of COS Θ is reduced. Consequently, it is possible to suppress the reduction in the amount of light in the peripheral portion of the image pickup range.

When conditional expression (3) is not satisfied, a light ray is incident obliquely on the light-receiving surface. Consequently, there is a reduction in the amount of light in the peripheral portion of the image pickup range.

It is preferable that one of the following conditional expressions (2') or (2") be satisfied instead of conditional expression (2).

$$0.8 < |PS \times Rimg| < 1.3 \tag{2'}$$

$$0.85 < |PS \times Rimg| < 1.0 \tag{2''}$$

It is preferable that the following conditional expression (3') be satisfied instead of conditional expression (3).

$$0.8 < |EXP/Rimg| < 1.3 \tag{3'}$$

In the image pickup apparatus of the present embodiment, it is preferable that the aperture stop be either disposed on a lens surface on the object side of the second lens or disposed on a lens surface on the image side of the second lens.

The second lens is positioned at a substantial center of the image forming optical system. Consequently, by making the abovementioned arrangement, the aperture stop assumes a state of being positioned near the center of the image forming optical system.

In this state, for instance, a lens surface which is convex toward the object side is provided on the object side of the apertures stop, and a lens surface which is convex toward the image side is provided on the image side of the aperture stop. By making such arrangement, it is possible to improve symmetry of arrangement of the lens surfaces. As a result, it is possible to suppress an occurrence of an off-axis aberration, such as an occurrence of a chromatic aberration of magnification.

The aperture stop includes an opening portion through which a light is transmitted, and a light-shielding portion which shields light. In many cases, the opening portion and the light-shielding portion are positioned in plane orthogonal to the optical axis. However, in the image pickup apparatus of the present embodiment, the second lens is cemented to the first lens and the third lens. Consequently, the opening portion and the light-shielding portion are positioned along a cemented surface.

In the image pickup apparatus of the present embodiment, for instance, the opening portion and the light-shielding portion are formed from an apex of a lens surface of the second lens toward a periphery. In this case, a center of the opening portion coincides with the apex of the lens surface. By cementing the second lens to the first lens and the third lens, the aperture stop is formed on the cemented surface.

In the image pickup apparatus of the present embodiment, it is preferable that at least one of a cemented surface of the first lens and the second lens in the cemented lens, a cemented surface of the second lens and the third lens in the cemented lens, and an image-side surface of the third lens, be an aspherical surface.

By making such arrangement, it is possible to suppress an occurrence of an aberration such as a spherical aberration, a coma, and an astigmatism.

In the image pickup apparatus of the present embodiment, it is preferable that a lens surface on the image side of the first lens be a surface which is convex toward the object side, and the following conditional expressions (4) and (5) be satisfied:

$$0 \leq |R1R/R1L| < 0.2 \tag{4}$$

and $$0.25 < R1R/f < 0.5 \tag{5}$$

where,

R1R denotes a paraxial radius of curvature of a lens surface on the image side, of the first lens, R1L denotes a paraxial radius of curvature of a lens surface on the object side, of the first lens, and f denotes a focal length for a d-line of the image forming optical system.

By letting the lens surface on the image side of the first lens to be a surface which is convex toward the object side, even when the angle of view is not less than 90 degrees for example, it is possible to secure a favorable imaging performance from a central portion up to a peripheral portion of the image pickup range.

When conditional expression (4) is not satisfied, either a curvature of the image-side surface of the first lens becomes small or a curvature of the object-side surface of the first lens becomes large.

Moreover, when conditional expression (5) is not satisfied, in a case of exceeding an upper value, the curvature of the image-side surface of the first lens becomes gentle. In this case, since a negative refractive power of the first lens becomes excessively small, a favorable image formation becomes difficult at the angle of view not less than 90 degrees. In a case of falling below a lower limit value of conditional expression (5), since the curvature of the image-side surface of the first lens becomes sharp, the spherical aberration and the coma are deteriorated.

In the image pickup apparatus of the present embodiment, it is preferable that the following conditional expression (6) be satisfied:

$$0 \leq |SAGs1/TL| < 0.05 \quad (6)$$

where,

SAGs1 denotes a distance in a direction along an optical axis, from a surface apex of the lens surface on the object side of the first lens up to a point in which a most peripheral effective light ray incident at the maximum image height on the image forming optical system passes through the lens surface on the object side of the first lens, letting a direction in which a light ray travels to be a direction with a positive sign, and TL denotes a distance on the optical axis, from the lens surface on the object side of the first lens up to the light-receiving surface.

The lens surface on the object side of the first lens is in contact with an external field. Therefore, according to an environment in which the image pickup apparatus is used, there is a possibility that a liquid and dirt etc. are adhered to the lens surface on the object side of the first lens. Consequently, the lens surface on the object side of the first lens is more susceptible to become dirty as compared to other lens surfaces.

Moreover, there is a possibility that the lens surface on the object side of the first lens comes in contact with an object around the image pickup apparatus. Consequently, the lens surface on the object side of the first lens is more susceptible to have a large impact as compared to other lens surfaces.

Therefore, in the image pickup apparatus of the present embodiment, the lens surface on the object side of the first lens is let to be a plane or to have a substantially plane shape that satisfies conditional expression (6). By making such arrangement, it is possible to make an arrangement such that the dirt is not adhered easily, or to make it stronger against an impact from an outside.

Moreover, even in a case in which the angle of view has become wide, it is possible to make an arrangement such that the apparent stop diameter does not become narrow. AS a result, it is possible to suppress a light fall-off at a peripheral portion of the image pickup range.

Moreover, it is possible to make an effective diameter of the image forming optical system small with respect to the image height or a size of an image pickup surface. Consequently, it is possible to make the optical system small-sized.

Moreover, even when the angle of view is not less than 90 degrees, it is possible to secure a favorable optical performance from the central portion up to the peripheral portion of the image pickup range.

When conditional expression (6) is not satisfied, it becomes difficult to secure a favorable imaging performance from the central portion up to the peripheral portion of the image pickup range. Particularly, in a case of widening the angle of view of the image forming optical system, it becomes difficult to secure a favorable imaging performance at the angle of view not less than 90 degrees.

The first lens is held by a frame member. For protecting the first lens, protrusion of the first lens toward the object side, with respect to the frame member may be made as small as possible. When the protrusion is large, the first lens and an object around the image pickup apparatus are susceptible to come in contact.

When a contact between the first lens and an object occurs, there is a possibility of the lens surface getting scratched due to an impact at the time of contact. Moreover, when the impact at the time of contact is heavy, there is a possibility that the lens surface is damaged.

For such reason, it is preferable to make an arrangement such that the contact between the first lens and an object does not occur as far as possible. For this, an arrangement is to be made such that the lens surface of the first lens does not protrude out from the frame member. In other words, the frame member is to be made to protrude toward the object side, with respect to the lens surface.

However, when the protrusion of the frame member with respect to the lens surface is made large, a light ray that was incident on the lens surface in design is shielded by the frame member. Moreover, a dent is formed at a boundary of the frame member and the lens surface, and water and dirt are accumulated in this dent.

In such manner, the protrusion of the frame member with respect to the lens surface becoming excessively large causes degradation of the quality of image.

As mentioned above, TL is the distance on the optical axis, from the lens surface on the object side of the first lens, up to the light-receiving surface. No air conversion is carried out while calculating this distance.

It is preferable that the following conditional expression (6') be satisfied instead of conditional expression (6).

$$0 \leq |SAGs1/TL| < 0.02 \quad (6')$$

In the image pickup apparatus according to the present embodiment, it is preferable that the second lens be a meniscus lens of which a convex surface is directed toward the object side, and the following conditional expression (7) is satisfied:

$$0.02 < THI2/TL < 0.2 \quad (7)$$

where,

THI2 denotes a distance on the optical axis, between surfaces of the second lens, and TL denotes the distance on the optical axis, from the lens surface on the object side of the first lens up to the light-receiving surface.

By letting the second lens to be the meniscus lens having a convex surface directed toward the object side, it is possible to realize small-sizing of the optical system while correcting a chromatic aberration.

In a case of exceeding an upper limit value of conditional expression (7), since a thickness of the second lens becomes excessively thick, the optical system becomes large-sized. In a case of falling below a lower limit value of conditional expression (7), the thickness of the second lens becomes excessively thin. Consequently, a refraction effect of the second lens is weakened.

It is preferable that the following conditional expression (7') be satisfied instead of conditional expression (7).

$$0.02 < THI2/TL < 0.1 \quad (7')$$

In the image pickup apparatus of the present embodiment, it is preferable that the third lens be a biconvex lens, and the following conditional expression (8) be satisfied:

$$-1 < (R3L+R3R)/(R3L-R3R) < 0 \quad (8)$$

where,

R3L denotes a paraxial radius of curvature of a lens surface on the object side, of the third lens, and R3R denotes a paraxial radius of curvature of a lens surface on the image side of, the third lens.

By letting the third lens to be the biconvex lens, it is possible to suppress the occurrence of astigmatism. Moreover, by letting the paraxial radius of curvature of the lens surface on the object side to be smaller than the paraxial radius of curvature of the lens surface on the image side, and by satisfying conditional expression (8), it is possible to suppress further the occurrence of astigmatism.

In a case of not satisfying conditional expression (8), it becomes difficult to suppress the occurrence of astigmatism.

When an attempt is made to widen the angle of view of the image forming optical system, a focal length of the image forming optical system becomes short. For shortening the focal length of the image forming optical system, it is necessary to make large a refractive power of the third lens which is a positive lens. However, when the refractive power of the third lens is made large, the astigmatism is susceptible to occur.

Making the paraxial radius of curvature of the lens surface on the object side smaller than the paraxial radius of curvature of the lens surface on the image side, as well as satisfying conditional expression (8) are effective for achieving both an increase in the refractive power of the third lens and correction of astigmatism. In other words, by making such arrangement, it is possible to widen the angle of view of the image forming optical system while suppressing the occurrence of astigmatism.

It is preferable that the following conditional expression (8') be satisfied instead of conditional expression (8).

$$-0.5 < (R3L+R3R)/(R3L-R3R) < 0 \quad (8')$$

In the image pickup apparatus of the present embodiment, it is preferable that the following conditional expression (9) be satisfied:

$$0.7 < |\Theta out60/\Theta img60| < 1.5 \quad (9)$$

$\Theta out60$ denotes the angle made by the predetermined principal light ray incident from the image-side surface of the third lens and the optical axis, $\Theta img60$ denotes an angle made by a straight line connecting two predetermined points and the optical axis, and here the predetermined principal light ray is a principal light ray for which an angle made with the optical axis is 60° in the space on the object side of the first lens, and the two predetermined points are a point of intersection of a predetermined principal light ray emerged from the image-side surface of the third lens and the light-receiving surface, and a center of curvature of the light-receiving surface.

By arranging the image forming optical system to satisfy conditional expression (9), it is possible to let a curvature in a meridional direction and a curvature in a sagittal direction to almost coincide, for a principal light ray of each image height. Consequently, it is possible to suppress the occurrence of astigmatism.

In a case of not satisfying conditional expression (9), it is not possible to let the curvature in the meridional direction and the curvature in the sagittal direction to coincide, for the principal light ray of each image height. Consequently, it becomes difficult to suppress the occurrence of astigmatism.

Here, it is possible to calculate $\Theta img60$ from the following expression.

$$\Theta img60 = a\sin(IM60/Rimg)$$

where,

IM60 denotes a distance from a point of intersection of a predetermined principal light ray emerged from the image-side surface of the third lens and the light-receiving surface, up to the optical axis, and Rimg denotes the radius of curvature of the virtual spherical surface which includes the surface apex and the point in which the principal light ray incident at the maximum angle of view on the image forming optical system intersects the light-receiving surface, letting the point of intersection of the optical axis and the light-receiving surface to be the surface apex.

It is preferable that the following conditional expression (9') or the conditional expression (9") be satisfied instead of conditional expression (9).

$$0.8 < |\Theta out60/\Theta img60| < 1.3 \quad (9')$$

$$0.85 < |\Theta out60/\Theta img60| < 1.25 \quad (9")$$

In the image pickup apparatus of the present embodiment, it is preferable that the second lens be a resin lens.

In a case of letting the second lens to be a resin lens, it is possible to make small a surface-shape error and a decentering error by making the second lens to be cured upon bringing in close contact with a refracting surface of the first lens. Furthermore, it is possible to make the image forming optical system thin.

For curing upon bringing in close contact, it is preferable to use a liquid resin such as an ultraviolet-cured resin. An ultraviolet-cured resin is an example of a lens material for the first lens. A desired amount of the ultraviolet-cured resin is to be discharged on to the refracting surface of the second lens. Accordingly, the ultraviolet-cured resin assumes a state of being in contact with the refracting surface of the second lens. Out of the surfaces of the ultraviolet-cured resin, a surface in contact with the refracting surface of the second lens becomes one refracting surface of the first lens.

A mold is disposed at a position facing the second lens holding the ultraviolet-cured resin. The mold is pressed against the ultraviolet-cured resin. The ultraviolet-cured resin is in a state of being held between the mold and the second lens. In this state, ultraviolet rays are irradiated from the second lens side. Accordingly, the ultraviolet-cured resin is cured.

The mold has a molding surface. The molding surface is a surface in contact with the ultraviolet-cured resin. A shape of the molding surface is same as a shape of the other refracting surface of the first lens. Out of the surfaces of the ultraviolet-cured resin, a surface in contact with the molding surface is the other refracting surface of the first lens.

In such manner, in curing upon bringing in close contact, one refracting surface of the first lens is formed by the refracting surface of the second lens, and the other refracting surface of the first lens is formed by the molding surface of the mold.

The material of the first lens is not restricted to the ultraviolet-cured resin. The method for curing is also not restricted to by irradiating the ultraviolet rays.

As it is evident from the description above, in the present embodiment, the cemented lens includes not only a cemented lens in which a plurality of lenses is cemented with an adhesive, but also a cemented lens in which lenses make a direct contact.

In the resin lens, as the thickness becomes thicker, the lens is more susceptible to an effect of a change in temperature and a change in humidity. Moreover, in a resin lens in which an ultraviolet-curing resin is used, as the thickness becomes thicker, it is hard to cure. In the resin lens, as the thickness becomes thinner, it is difficult to stick.

For such reasons, in a case of letting the second lens to be a resin lens, it is preferable to satisfy the abovementioned conditional expression (7). By satisfying conditional expression (7), it is possible to reduce an effect due to the change in temperature and an effect due to the change in humidity, and to improve the curability and adhesiveness.

In the image pickup apparatus of the present embodiment, it is preferable that the lens surface on the object side, of the first lens be either a plane surface or a surface which is convex toward the object side.

By letting the lens surface on the object side of the first lens to be a surface which is convex toward the object side, it is possible to make small an angle made by a light ray incident on the lens surface on the object side and a normal of the lens surface. Consequently, it is possible to suppress occurrence of various aberrations such the astigmatism, a distortion, and the coma.

It is preferable that the image pickup apparatus of the present embodiment further include an illuminating section, and a cover portion which is disposed on the object side of the image forming optical system.

By disposing the cover portion, it is possible to make an arrangement such that a distance between an object and the image forming optical system is not close excessively, and it is useful for letting the object to be within a depth of field. By including the illuminating section, it becomes useful for night photography and intracavitary photography.

In the image pickup apparatus of the present embodiment, it is preferable that the cover portion be a cover portion having a dome shape covering both of the image forming optical system and the illuminating section.

By making such arrangement, it is possible to make an arrangement such that a distance between the object and the illuminating section is not excessively close, and to reduce an overexposure of a photographic image.

It is preferable that an optical apparatus of the present invention include an image pickup apparatus and an illuminating section.

Since an image pickup apparatus of each embodiment is small in size, it is possible to make the optical apparatus small-sized.

It is preferable that the optical apparatus of the present embodiment includes a dome-shaped cover portion which is disposed on the object side of the image forming optical system and the illuminating section.

By making such arrangement, it is possible to use the optical apparatus as a capsule endoscope.

It is preferable that the optical apparatus of the present embodiment include an insertion section, in which a through hole is formed, and a length of the insertion section be longer as compared to a diameter of the through hole, and the image forming optical system and the illuminating section be disposed inside the through hole.

By making such arrangement, it is possible to use the optical apparatus as a flexible endoscope and as a rigid endoscope.

In the optical apparatus of the present embodiment, it is preferable that the insertion section include two image forming optical systems which are disposed in parallel, and the two image forming optical systems be disposed at a predetermined interval, and the predetermined interval be set to be such that there is a parallax.

By making such arrangement, it is possible to realize an optical apparatus in which a stereoscopic vision is possible.

Examples of the image pickup apparatus and the capsule endoscope according to certain aspects of the present invention are described below in detail by referring to the accompanying diagrams. However, the present invention is not restricted to the examples described below.

Cross-sectional views will be described below. FIG. 1A, FIG. 2A, FIG. 3A, FIG. 4A, FIG. 5A, FIG. 6A, and FIG. 7A show lens cross-sections.

Aberration diagrams will be described below.

FIG. 1B, FIG. 2B, FIG. 3B, FIG. 4B, FIG. 5B, FIG. 6B, and FIG. 7B show a spherical aberration (SA).

FIG. 1C, FIG. 2C, FIG. 3C, FIG. 4C, FIG. 5C, FIG. 6C, and FIG. 7C show an astigmatism (AS).

FIG. 1D, FIG. 2D, FIG. 3D, FIG. 4D, FIG. 5D, FIG. 6D, and FIG. 7D show a distortion (DT).

FIG. 1E, FIG. 2E, FIG. 3E, FIG. 4E, FIG. 5E, FIG. 6E, and FIG. 7E show a chromatic aberration of magnification (CC).

An image forming optical system of an image pickup apparatus of an example 1 includes in order from an object side, a negative meniscus lens L1 having a convex surface directed toward the object side, a negative meniscus lens L2 having a convex surface directed toward the object side, and a biconvex positive lens L3. The negative meniscus lens L1, the negative meniscus lens L2, and the biconvex positive lens L3 are cemented.

An aperture stop S is disposed on an object-side surface of the negative meniscus lens L2. The negative meniscus lens L2 is cemented to the negative meniscus lens L1. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the negative meniscus lens L2, a cemented surface of the negative meniscus lens L2 and the biconvex positive lens L3, and an image-side surface of the biconvex positive lens L3.

An image forming optical system of an image pickup apparatus of an example 2 includes in order from an object side, a negative meniscus lens L1 having a convex surface directed toward the object side, a negative meniscus lens L2 having a convex surface directed toward the object side, and a biconvex positive lens L3. The negative meniscus lens L1, the negative meniscus lens L2, and the biconvex positive lens L3 are cemented.

An aperture stop S is disposed on an image-side surface of the negative meniscus lens L2. The negative meniscus lens L2 is cemented to the biconvex positive lens L3. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the negative meniscus lens L2, a cemented surface of the negative meniscus lens L2 and the biconvex positive lens L3, and an image-side surface of the biconvex positive lens L3.

An image forming optical system of an image pickup apparatus of an example 3 includes in order from an object side, a negative meniscus lens L1 having a convex surface directed toward the object side, a positive meniscus lens L2 having a convex surface directed toward the object side, and a biconvex positive lens L3. The negative meniscus lens L1, the positive meniscus lens L2, and the biconvex positive lens L3 are cemented.

An aperture stop S is disposed on an object-side surface of the positive meniscus lens L2. The positive meniscus lens L2 is cemented to the negative meniscus lens L1. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the positive meniscus lens L2, a cemented surface of the positive meniscus lens L2 and the biconvex positive lens L3, and an image-side surface of the biconvex positive lens L3.

An image forming optical system of an image pickup apparatus of an example 4 includes in order from an object side, a negative meniscus lens L1 having a convex surface directed toward the object side, a positive meniscus lens L2 having a convex surface directed toward the object side, and a biconvex positive lens L3. The negative meniscus lens L1, the positive meniscus lens L2, and the biconvex positive lens L3 are cemented.

An aperture stop S is disposed on an image-side surface of the positive meniscus lens L2. The positive meniscus lens L2 is cemented to the biconvex positive lens L3. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the positive meniscus lens L2, a cemented surface of the positive meniscus lens L2 and the biconvex positive lens L3, and an image-side surface of the biconvex positive lens L3.

An image forming optical system of an image pickup apparatus of an example 5 includes in order from an object side, a negative meniscus lens L1 having a convex surface directed toward the object side, a positive meniscus lens L2 having a convex surface directed toward the object side, and a biconvex positive lens L3. The negative meniscus lens L1, the positive meniscus lens L2, and the biconvex positive lens L3 are cemented.

An aperture stop S is disposed on an image side-surface of the positive meniscus lens L2. The positive meniscus lens L2 is cemented to the biconvex positive lens L3. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the positive meniscus lens L2, a cemented surface of the positive meniscus lens L2 and the biconvex positive lens L3, and an image-side surface of the biconvex positive lens L3.

An image forming optical system of an image pickup apparatus of an example 6 includes in order from an object side, a planoconcave negative lens L1, a positive meniscus lens L2 having a convex surface directed toward the object side, and a biconvex positive lens L3. The planoconcave negative lens L1, the positive meniscus lens L2, and the biconvex positive lens L3 are cemented.

An aperture stop S is disposed on an image-side surface of the positive meniscus lens L2. The positive meniscus lens L2 is cemented to the biconvex positive lens L3. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to three surfaces which are, a cemented surface of the planoconcave negative lens L1 and the positive meniscus lens L2, a cemented surface of the positive meniscus lens L2 and the biconvex positive lens L3, and an image-side surface of the biconvex positive lens L3.

An image forming optical system of an image pickup apparatus of an example 7 includes in order from an object side, a negative meniscus lens L1 having a convex surface directed toward the object side, a positive meniscus lens L2 having a convex surface directed toward the object side, and a biconvex positive lens L3. The negative meniscus lens L1, the positive meniscus lens L2, and the biconvex positive lens L3 are cemented.

An aperture stop S is disposed on an image-side surface of the positive meniscus lens L2. The positive meniscus lens L2 is cemented to the biconvex positive lens L3. Consequently, the aperture stop S is formed on a cemented surface. More specifically, an opening portion and a light-shielding portion are formed from an apex of the cemented surface toward a periphery. A light-receiving surface (image pickup surface) I is a spherical surface, and is curved to be concave toward the object side.

An aspherical surface is provided to four surfaces which are, an object-side surface of the negative meniscus lens L1, a cemented surface of the negative meniscus lens L1 and the positive meniscus lens L2, a cemented surface of the positive meniscus lens L2 and the biconvex positive lens L3, and an image-side surface of the biconvex positive lens L3.

Figure 8:
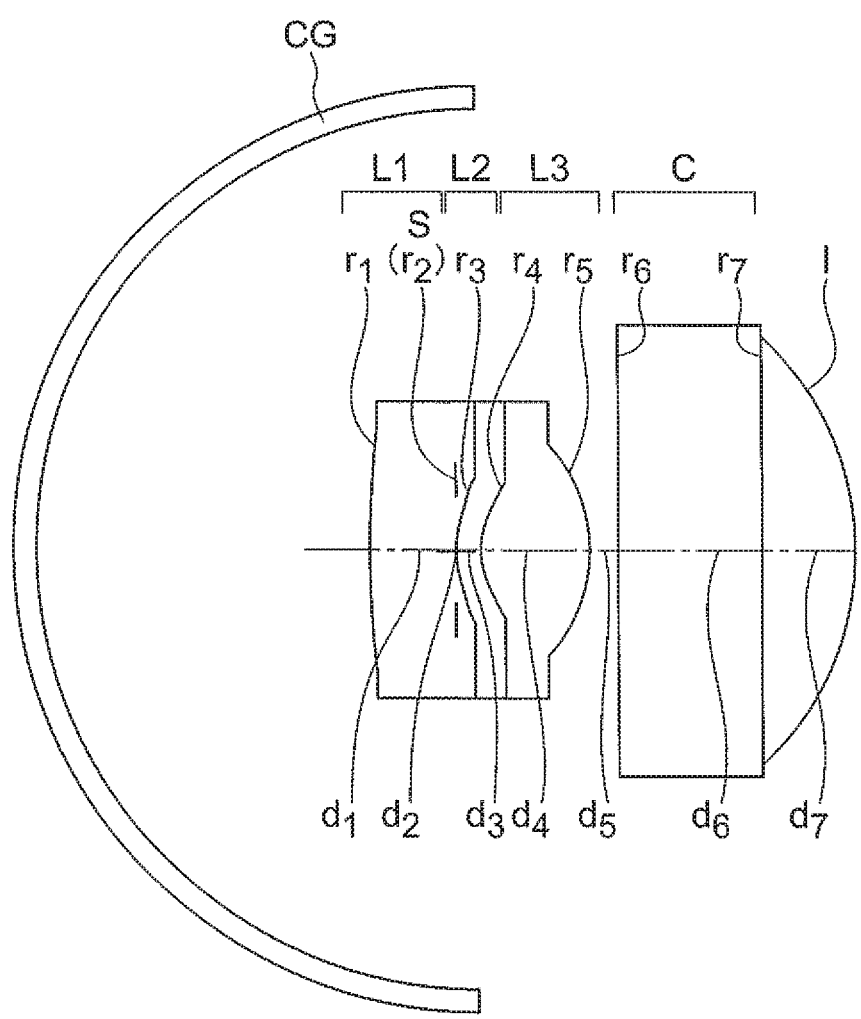
FIG. 8 is a cross-sectional view of an image forming optical system according to an example 8.

An image forming optical system according to an example 8, as shown in FIG. 8, includes in order from an object side, an optical member CG, a negative meniscus lens L1 having a convex surface directed toward the object side, a negative meniscus lens L2 having a convex surface directed toward the object side, and a biconvex positive lens L3. The optical system including the negative meniscus lens L1, the negative meniscus lens L2, an aperture stop S, and the biconvex positive lens L3 is same as the optical system according to the example 1.

FIG. 8 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 8, both the object-side surface and the image-side surface being curved surfaces, an overall shape of the optical member CG is hemispherical. In the example 8, a thickness of the optical member CG, or in other words, a distance between the object-side surface and the image-side surface, is constant. However, the thickness of the optical member CG may not be constant.

Moreover, as it will be described later, the optical member CG is disposed at a position only 6.0 mm away on the object side from the object-side surface of the first lens. However, the optical member CG may be disposed at a position shifted frontward or rearward from the abovementioned position. Moreover, a radius of curvature and the thickness of the optical member CG mentioned here is an example, and are not limited to the radius of curvature and the thickness mentioned here.

A material that allows light to transmit through has been used for the optical member CG. Consequently, light from an object passes through the optical member CG and is incident on the negative meniscus lens L1. The optical member CG is disposed such that a curvature center of the image-side surface substantially coincides with a position of an entrance pupil. Consequently, a new aberration due to the optical member CG hardly occurs. In other words, an imaging performance of the image forming optical system according to the example 8 is not different from an imaging performance of the image forming optical system according to the example 1.

The optical member CG functions as a cover glass. In this case, the optical member CG corresponds to an observation window provided at an outer covering of a capsule endoscope. Therefore, the image forming optical system according to the example 8 can be used for an optical system of a capsule endoscope. The image forming optical systems according to the example 1 to the example 7 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, *denotes an aspherical surface, and stop denotes an aperture stop.

Further, in Various data, f denotes a focal length of the entire system, FNO. denotes an F number, ω denotes a half angle of view, IH denotes an image height.

Moreover, the example 8 is an example in which, the optical member CG is disposed on the object side of the image forming optical system according to the example 1. In surface data of the example 8, C1 denotes the object-side surface of the optical member CG and C2 denotes the image-side surface of the optical member CG. Aspherical surface data and various data of the example 8 being same as the aspherical surface data and various data of the example 1, description thereof is omitted here.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10

$$Z=(y^2/r)/[1+\{1-(1+k)(y/r)^2\}^{1/2}]+A4y^4+A6y^6+A8y^8+A10y^{10}$$

Further, in the aspherical surface coefficients, 'e-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | vd |
| Object plane | ∞ | 10.00 | | |
| 1* | 3.915 | 0.30 | 1.51633 | 64.14 |
| 2 (Stop) | ∞ | 0.00 | | |
| 3* | 0.341 | 0.08 | 1.63387 | 23.38 |
| 4* | 0.264 | 0.38 | 1.59201 | 67.02 |
| 5* | −0.541 | 0.10 | | |
| 6 | ∞ | 0.50 | 1.51633 | 64.14 |
| 7 | ∞ | 0.32 | | |
| Image plane | −1.021 | | | |

Aspherical surface data

1st surface k = 0.000
A4 = 1.01078e−02, A6 = 3.57526e−01
3rd surface k = 0.000
A4 = −1.50834e+01, A6 = −8.56121e+01, A8 = 2.20481e+03
4th surface k = 0.000
A4 = −1.50424e+01, A6 = 1.11831e+01, A8 = −1.73879e+03
5th surface k = 0.000
A4 = −1.09574e−01, A6 = 8.90158e−01, A8 = −2.24239e+01,
A10 = 1.37860e+02

| Various data | |
|---|---|
| f | 0.78 |
| FNO. | 2.86 |
| 2ω | 140.00 |
| IH | 0.73 |

Example 2

| Unit mm | | | | |
|---|---|---|---|---|
| Surface data | | | | |
| Surface no. | r | d | nd | vd |
| Object plane | ∞ | 10.00 | | |
| 1* | 4.119 | 0.30 | 1.51633 | 64.14 |
| 2* | 0.336 | 0.09 | 1.63387 | 23.38 |
| 3 (Stop) | ∞ | 0.00 | | |
| 4* | 0.273 | 0.38 | 1.59201 | 67.02 |
| 5* | −0.544 | 0.10 | | |
| 6 | ∞ | 0.50 | 1.51633 | 64.14 |
| 7 | ∞ | 0.32 | | |
| Image plane | −1.010 | | | |

-continued

Unit mm

Aspherical surface data

1st surface k = 0.000
A4 = 9.12915e−02, A6 = 7.41213e−02
2nd surface k = 0.000
A4 = −1.28745e+01, A6 = −1.27825e+02, A8 = 1.07474e+03
4th surface k = 0.000
A4 = −7.32807e+00, A6 = −1.28401e+01, A8 = −3.30868e+03
5th surface k = 0.000
A4 = −2.38483e−01, A6 = 7.37942e−01, A8 = −1.97726e+01,
A10 = 9.25956e+01

Various data

| | |
|---|---|
| f | 0.79 |
| FNO. | 2.85 |
| 2ω | 140.00 |
| IH | 0.73 |

Example 3

Unit mm

Surface data

| Surface no. | r | d | nd | vd |
|---|---|---|---|---|
| Object plane | ∞ | 10.00 | | |
| 1* | 5.478 | 0.30 | 1.51633 | 64.14 |
| 2 (Stop) | ∞ | 0.00 | | |
| 3* | 0.339 | 0.11 | 1.63387 | 23.38 |
| 4* | 0.421 | 0.38 | 1.59201 | 67.02 |
| 5* | −0.558 | 0.10 | | |
| 6 | ∞ | 0.50 | 1.51633 | 64.14 |
| 7 | ∞ | 0.32 | | |
| Image plane | −1.043 | | | |

Aspherical surface data

1st surface k = 0.000
A4 = −2.73993e−02, A6 = 3.59800e−01
3rd surface k = 0.000
A4 = −7.34591e+00, A6 = −1.35791e+02, A8 = 1.25398e+03
4th surface k = 0.000
A4 = 1.12022e+01, A6 = −2.39954e+02, A8 = 1.34059e+03
5th surface k = 0.000
A4 = −2.13402e−01, A6 = 2.46455e+00, A8 = −2.31632e+01,
A10 = 3.21745e+01

Various data

| | |
|---|---|
| f | 0.79 |
| FNO. | 2.90 |
| 2ω | 140.00 |
| IH | 0.73 |

Example 4

Unit mm

Surface data

| Surface no. | r | d | nd | vd |
|---|---|---|---|---|
| Object plane | ∞ | 10.00 | | |
| 1* | 5.245 | 0.30 | 1.51633 | 64.14 |
| 2* | 0.339 | 0.12 | 1.63387 | 23.38 |
| 3 (Stop) | ∞ | 0.00 | | |
| 4* | 0.408 | 0.38 | 1.59201 | 67.02 |
| 5* | −0.559 | 0.10 | | |
| 6 | ∞ | 0.50 | 1.51633 | 64.14 |
| 7 | ∞ | 0.32 | | |
| Image plane | −1.045 | | | |

Aspherical surface data

1st surface k = 0.000
A4 = −1.65174e−03, A6 = 1.05156e−01
2nd surface k = 0.000
A4 = −7.06981e+00, A6 = −3.94640e+01, A8 = −2.78628e+02
4th surface k = 0.000
A4 = 1.61345e+01, A6 = −2.05251e+02, A8 = 3.98054e+03
5th surface k = 0.000
A4 = −3.01045e−01, A6 = 1.57960e+00, A8 = −2.81214e+01,
A10 = 3.76612e−01

Various data

| | |
|---|---|
| f | 0.79 |
| FNO. | 2.89 |
| 2ω | 140.00 |
| IH | 0.73 |

Example 5

Unit mm

Surface data

| Surface no. | r | d | nd | vd |
|---|---|---|---|---|
| Object plane | ∞ | 10.00 | | |
| 1* | 1.711 | 0.30 | 1.53367 | 55.82 |
| 2* | 0.249 | 0.06 | 1.63387 | 23.38 |
| 3 (Stop) | ∞ | 0.00 | | |
| 4* | 0.232 | 0.37 | 1.53367 | 55.82 |
| 5* | −0.440 | 0.10 | | |
| 6 | ∞ | 0.30 | 1.51633 | 64.14 |
| 7 | ∞ | 0.40 | | |
| Image plane | −0.903 | | | |

Aspherical surface data

1st surface k = 0.000
A4 = 1.90268e−01, A6 = 2.04812e−01
2nd surface k = 0.000
A4 = −4.45853e+01

-continued

| Unit mm | | | | |
|---|---|---|---|---|
| 4th surface | | | | |
| k = 0.000 | | | | |
| A4 = −2.75086e+01 | | | | |
| 5th surface | | | | |
| k = 0.000 | | | | |
| A4 = −2.20911e−01, A6 = −2.49190e+00 | | | | |

| Various data | |
|---|---|
| f | 0.76 |
| FNO. | 2.89 |
| 2ω | 140.00 |
| IH | 0.73 |

Example 6

| Unit mm | | | | |
|---|---|---|---|---|
| Surface data | | | | |
| Surface no. | r | d | nd | vd |
| Object plane | ∞ | 10.00 | | |
| 1 | ∞ | 0.30 | 1.51633 | 64.14 |
| 2* | 0.320 | 0.15 | 1.63387 | 23.38 |
| 3 (Stop) | ∞ | 0.00 | | |
| 4* | 0.359 | 0.38 | 1.59201 | 67.02 |
| 5* | −0.553 | 0.10 | | |
| 6 | ∞ | 0.50 | 1.51633 | 64.14 |
| 7 | ∞ | 0.32 | | |
| Image plane | −1.264 | | | |

| Aspherical surface data | |
|---|---|
| 2nd surface | |
| k = 0.000 | |
| A4 = −2.39160e+00, A6 = −1.64025e+02, A8 = 1.78226e+03 | |
| 4th surface | |
| k = 0.000 | |
| A4 = 2.44268e+01, A6 = −4.18708e−01, A8 = −6.12781e+03 | |
| 5th surface | |
| k = 0.000 | |
| A4 = −2.47671e−01, A6 = −2.58386e+00, A8 = −1.34562e+00, A10 = −4.60865e+02 | |

| Various data | |
|---|---|
| f | 0.81 |
| FNO. | 3.03 |
| 2ω | 140.00 |
| IH | 0.73 |

Example 7

| Unit mm | | | | |
|---|---|---|---|---|
| Surface data | | | | |
| Surface no. | r | d | nd | vd |
| Object plane | ∞ | 10.00 | | |
| 1* | 3.940 | 0.30 | 1.51633 | 64.14 |
| 2* | 0.312 | 0.11 | 1.63387 | 23.38 |

-continued

| Unit mm | | | | |
|---|---|---|---|---|
| 3 (Stop) | ∞ | 0.00 | | |
| 4* | 0.345 | 0.36 | 1.59201 | 67.02 |
| 5* | −0.535 | 0.10 | | |
| 6 | ∞ | 0.30 | 1.51633 | 64.14 |
| 7 | ∞ | 0.40 | | |
| Image plane | −0.963 | | | |

| Aspherical surface data | |
|---|---|
| 1st surface | |
| k = 0.000 | |
| A4 = −1.59904e−01, A6 = 1.67922e−01 | |
| 2nd surface | |
| k = 0.000 | |
| A4 = −9.76312e+00, A6 = 4.40264e+01, A8 = −1.53642e+03 | |
| 4th surface | |
| k = 0.000 | |
| A4 = 1.39889e+01, A6 = −2.57438e+01, A8 = −3.08758e+02 | |
| 5th surface | |
| k = 0.000 | |
| A4 = −2.85173e−01, A6 = 1.46899e+00, A8 = −3.49420e+01, A10 = −1.62304e+02 | |

| Various data | |
|---|---|
| f | 0.75 |
| FNO. | 2.95 |
| 2ω | 169.99 |
| IH | 0.73 |

Example 8

| Unit mm | | | | |
|---|---|---|---|---|
| Surface data | | | | |
| Surface no. | r | d | nd | vd |
| Object plane | ∞ | 3.50 | | |
| C1 | 8.500 | 0.50 | 1.5896 | 30.00 |
| C2 | 8.000 | 6.00 | | |
| 1* | 3.915 | 0.30 | 1.51633 | 64.14 |
| 2 (Stop) | ∞ | 0.00 | | |
| 3* | 0.341 | 0.08 | 1.63387 | 23.38 |
| 4* | 0.264 | 0.38 | 1.59201 | 67.02 |
| 5* | −0.541 | 0.10 | | |
| 6 | ∞ | 0.50 | 1.51633 | 64.14 |
| 7 | ∞ | 0.32 | | |
| Image plane | −1.021 | | | |

Next, values of conditional expressions in each example are given below.

| | Example 1 | Example 2 | Example 3 |
|---|---|---|---|
| (1) \|Θout60/60°\| | 0.64 | 0.70 | 0.61 |
| (2) \|PS × Rimg\| | 0.87 | 0.86 | 0.87 |
| (3) \|EXP/Rimg\| | 1.15 | 1.06 | 1.15 |
| (4) \|R1R/R1L\| | 0.09 | 0.08 | 0.06 |
| (5) R1R/f | 0.43 | 0.43 | 0.43 |
| (6) \|SAGs1/TL\| | 0.001 | 0.003 | 0.001 |
| (7) THI2/TL | 0.05 | 0.06 | 0.07 |
| (8) (R3L + R3R)/(R3L − R3R) | −0.34 | −0.33 | −0.14 |
| (9) \|Θout60/Θimg60\| | 0.91 | 1.00 | 0.90 |

-continued

|  | Example 4 | Example 5 | Example 6 |
|---|---|---|---|
| (1) $|\Theta out60/60°|$ | 0.70 | 0.73 | 0.66 |
| (2) $|PS \times Rimg|$ | 0.87 | 0.89 | 0.98 |
| (3) $|EXP/Rimg|$ | 1.02 | 1.15 | 0.85 |
| (4) $|R1R/R1L|$ | 0.06 | 0.15 | 0.00 |
| (5) $R1R/f$ | 0.43 | 0.33 | 0.39 |
| (6) $|SAGs1/TL|$ | 0.003 | 0.009 | 0.000 |
| (7) $THI2/TL$ | 0.07 | 0.04 | 0.09 |
| (8) $(R3L + R3R)/(R3L - R3R)$ | −0.16 | −0.31 | −0.21 |
| (9) $|\Theta out60/\Theta img60|$ | 1.03 | 0.91 | 1.22 |

|  | Example 7 |
|---|---|
| (1) $|\Theta out60/60°|$ | 0.70 |
| (2) $|PS \times Rimg|$ | 0.86 |
| (3) $|EXP/Rimg|$ | 1.04 |
| (4) $|R1R/R1L|$ | 0.08 |
| (5) $R1R/f$ | 0.42 |
| (6) $|SAGs1/TL|$ | 0.005 |
| (7) $THI2/TL$ | 0.07 |
| (8) $(R3L + R3R)/(R3L - R3R)$ | −0.22 |
| (9) $|\Theta out60/\Theta img60|$ | 1.00 |

Figure 9:
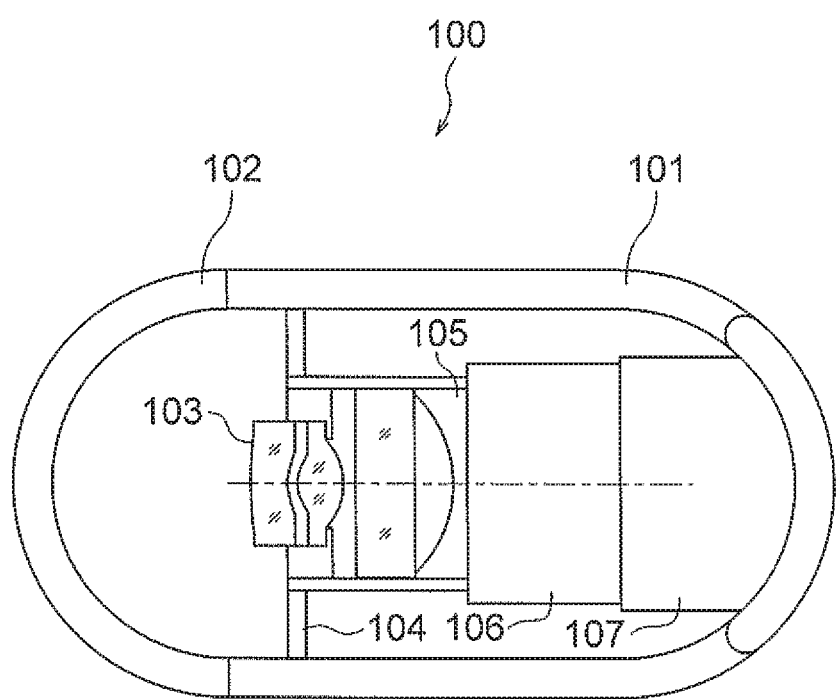
FIG. 9 is a diagram showing a schematic arrangement of a capsule endoscope.

FIG. 9 illustrates an example of an image pickup apparatus. In this example, the image pickup apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, a illumination unit 104, an image pickup element 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image pickup element 105. A drive and control of the image pickup element 105 is carried out by the drive control unit 106. Moreover, an output signal from the image pickup element 105 is processed by the signal processing unit 107 according to the requirement.

Here, for the image forming optical system. 103, the image forming optical system according to the abovementioned example 1 for instance, is used. In such manner, the image forming optical system 103 has a wide angle of view and a small F-number, while being small-sized. Consequently, in the image forming optical system 103, a wide-angle optical image having a high resolution is acquired.

Moreover, the capsule endoscope 100 includes an optical system having a long back focus and being capable of forming a favorable image, while being small-sized. Consequently, in the capsule endoscope 100, it is possible to acquire a wide-angle image with high resolution, while being small-sized.

Here, the image pickup element has a curved light-receiving surface. However, even when the light-receiving surface of the image pickup element is flat, if a surface which receives an image is curved, that surface can be referred to as a curved light-receiving surface. As an example, an arrangement in which a fiber bundle is disposed on a light-receiving surface of an image pickup element having a flat light-receiving surface, and one end-surface thereof is processed to have a curved shape, and an object image is received by that curved end-surface, is possible.

Figure 10A:
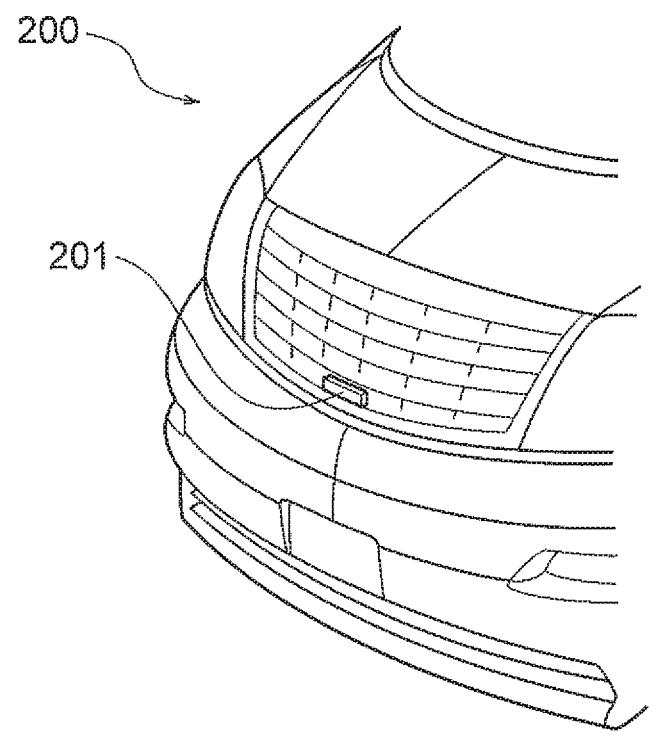
FIG. 10A and FIG. 10B are diagrams showing a car-mounted camera.
Figure 10B:
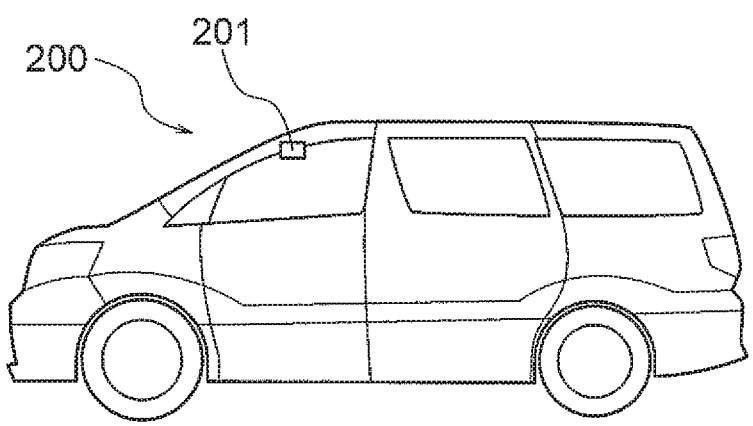

FIG. 10A and FIG. 10B are diagrams illustrating another example of an image pickup apparatus. In this example, the image pickup apparatus is a car-mounted camera. FIG. 10A is a diagram illustrating an example of a car-mounted camera mounted at an outside of a car, and FIG. 10B is a diagram illustrating an example of a car-mounted camera mounted inside a car.

As shown in FIG. 10A, a car-mounted camera 201 is provided to a front grill of an automobile 200. The car-mounted camera 201 includes an image forming optical system and an image pickup element. For the image forming optical system of the car-mounted camera 201, the image forming optical system according to the abovementioned example 1 is used. Consequently, a favorable optical image is formed.

As shown in FIG. 10B, the car-mounted camera 201 is provided near a ceiling of the automobile 200. An action and an effect of the car-mounted camera 201 are as have already been described. In the car-mounted camera 201, it is possible to acquire a wide-angle image with high resolution, while being small-sized.

Figure 11:
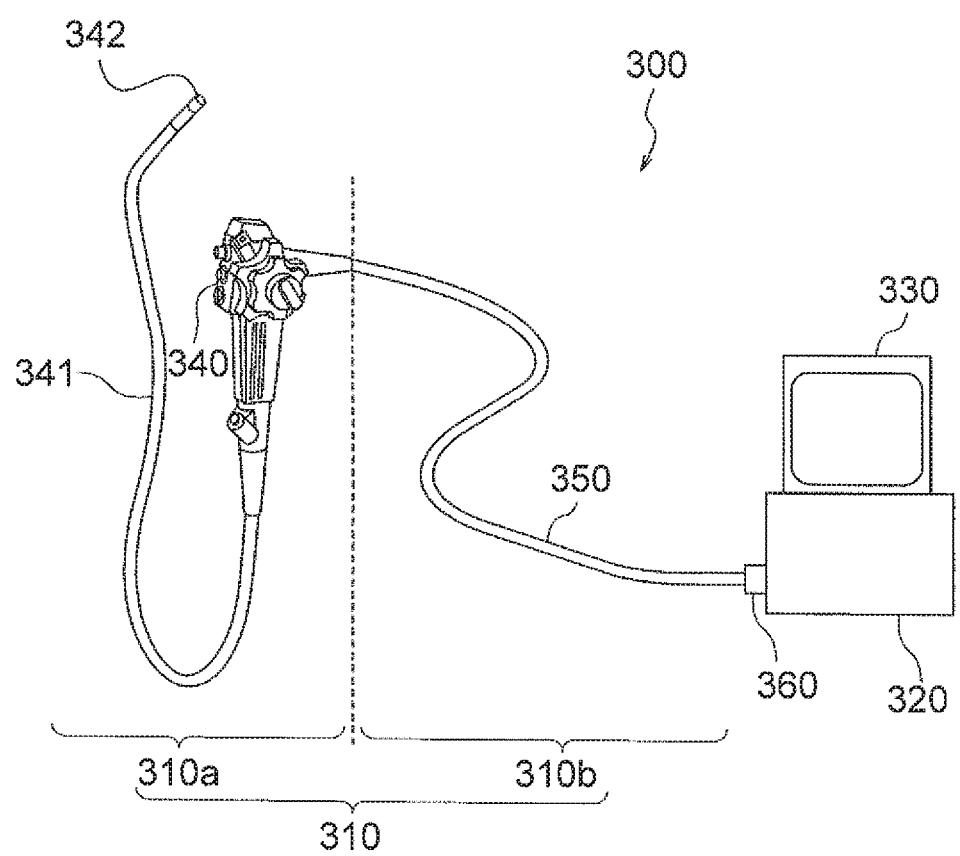
FIG. 11 is a diagram showing a schematic arrangement of an endoscope system.

FIG. 11 is a diagram illustrating another example of an image pickup apparatus. In this example, the image pickup apparatus is an endoscope system. FIG. 11 is a diagram showing a schematic arrangement of the endoscope system.

An endoscope system 300 is an observation system in which an electronic endoscope is used. The endoscope system 300 includes an electronic endoscope 310 and an image processing unit 320. The electronic endoscope 310 includes a scope section 310a and a connecting cord section 310b. Moreover, a display unit 330 is connected to the image processing unit 320.

The scope section 310a is mainly divided into an operating portion 340 and an inserting portion 341. The inserting portion 341 is long and slender, and can be inserted into a body cavity of a patient. Moreover, the inserting portion 341 is formed of a flexible member. An observer can carry out various operations by an angle knob that is provided to the operating portion 340.

Moreover, the connecting cord section 310 b is extended from the operating portion 340. The connecting cord section 301b includes a universal cord 350. The universal cord 350 is connected to the image processing unit 320 via a connector 360.

The universal cord 350 is used for transceiving of various types of signals. Various types of signals include signals such as a power-supply voltage signal and a CCD (charge coupled device) driving signal. These signals are transmitted from a power supply unit and a video processor to the scope section 310a. Moreover, various types of signals include a video signal. This signal is transmitted from the scope section 310a to the video processor.

Peripheral equipment such as a VTR (video tape recorder) deck and a video printer can be connected to the video processor inside the image processing unit 320. The video processor carries out signal processing on a video signal from the scope section 310a. On the basis of the video signal, an endoscope image is displayed on a display screen of the display unit 330.

Figure 12:
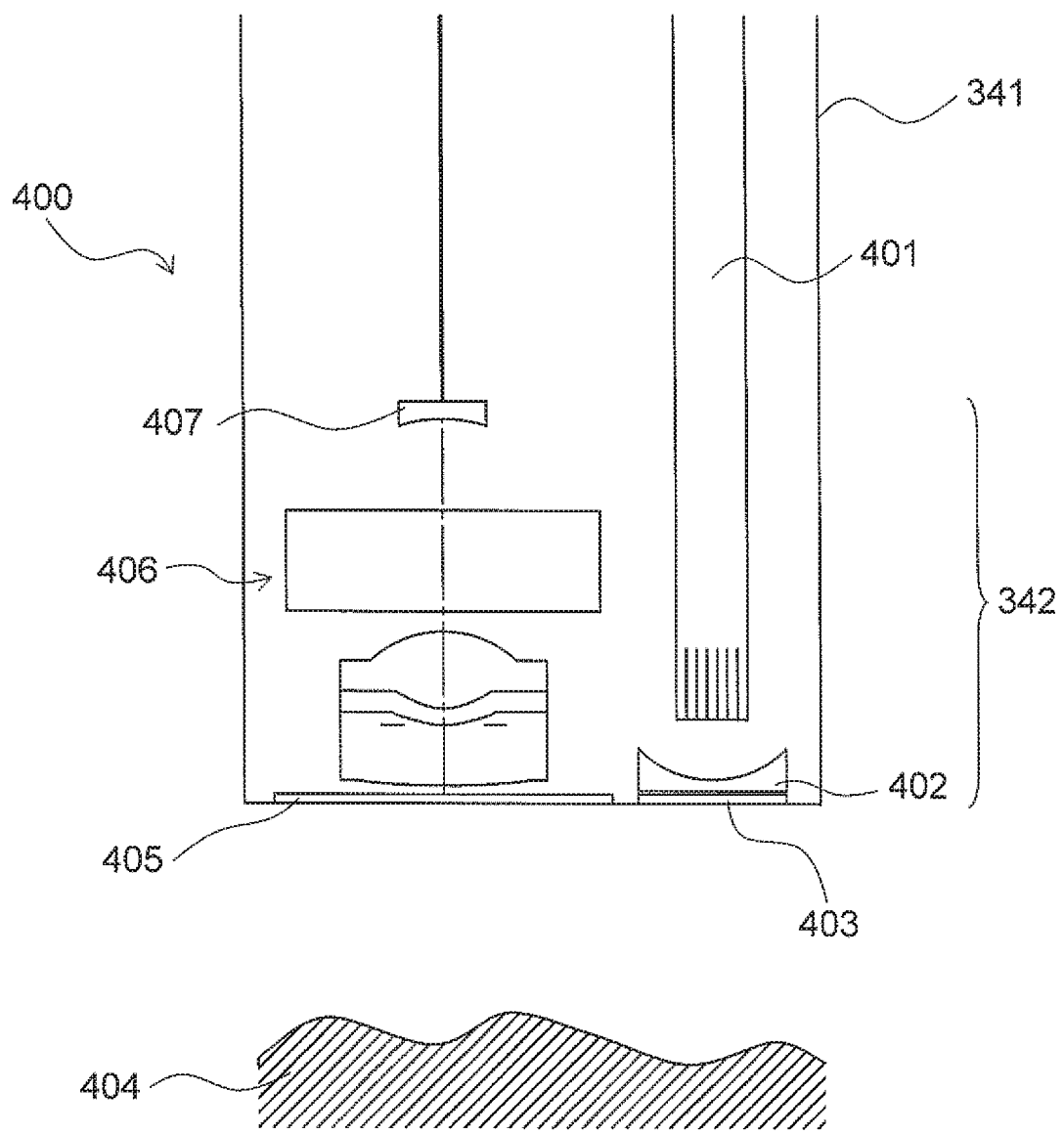
FIG. 12 is a diagram showing an arrangement of an optical system of an endoscope.

An optical system is disposed at a front-end portion 342 of the inserting portion 341. FIG. 12 is a diagram showing an arrangement of the optical system of the endoscope. An optical system 400 includes an illuminating section and an observation section.

The illuminating section includes a light guide 401 and an illumination lens 402. The light guide 401 transmits illumination light to a front-end portion 342 of an inserting portion 341. The illumination light transmitted emerges from a front-end surface of the light guide 401.

The illumination lens 402 is disposed at the front-end portion 342. The illumination lens 402 is disposed at a position facing a front-end surface of the light guide 401. The illumination light passes through the illumination lens 402, and emerges from an illumination window 403. Accordingly, a site to be observed inside a body to be examined (hereinafter, referred to as 'observation site 404') is illuminated.

In the front-end portion 342, an observation window 405 is provided adjacent to the illumination window 403. Light from the observation site 404 passes through the observation window 405, and is incident on the front-end portion 342. In a rear of the observation window 405, an observation section is provided.

The observation section includes an image forming optical system 406 and an image pickup element 407. For the image forming optical system 406, the image forming optical system of the example 1 is used.

Light reflected from the observation site 404 passes through the image forming optical system 406, and is incident on the image pickup element 407. An image (optical image) of the observation site 404 is formed on an image pickup surface of the image pickup element 407. The image of the observation site 404 is subjected to opto-electric conversion, and accordingly, an image of the observation site 404 is acquired. The image of the observation site 404 is displayed on a display unit 330. In such manner, an observer can observe the image of the observation site 404.

In the image forming optical system 406, an image plane has a curved shape. The image pickup element 407 has a light-receiving surface having a curved shape same as the shape of the image plane. By using the image pickup element 407, it is possible to improve an image quality of a photographic image.

In the front-end portion 342 shown in FIG. 12, since the number of image forming optical systems is one, the stereoscopic vision is not possible. The stereoscopic vision becomes possible by using two image forming optical systems.

Figure 13:
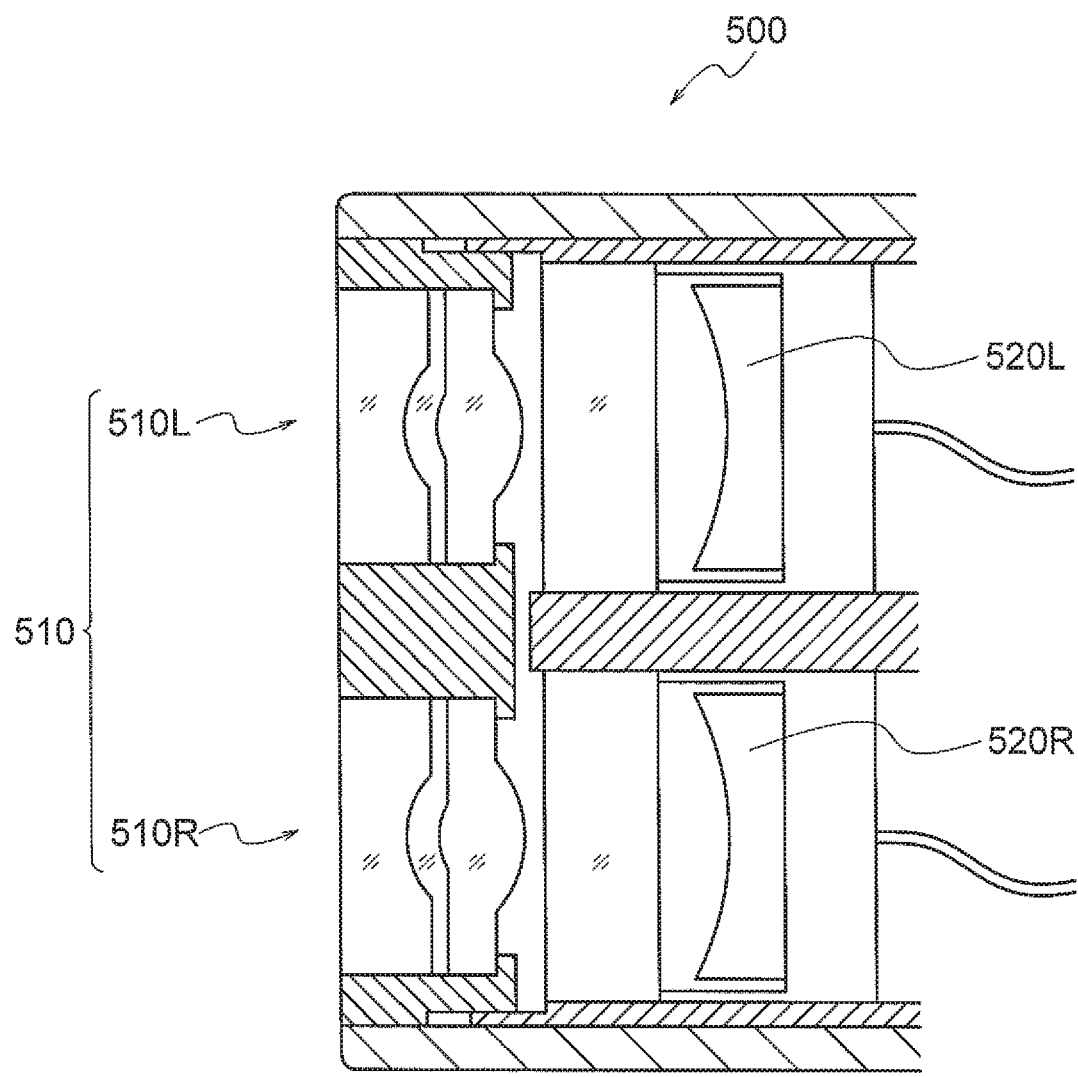
FIG. 13 is a diagram showing an arrangement of an optical system of a stereoscopic endoscope.

FIG. 13 is a diagram showing an arrangement of an optical system of a stereoscopic endoscope. An image forming optical system 510 is disposed in a front-end portion 500 of the stereoscopic endoscope. Although an illuminating optical system is also disposed in the front-end portion 500, it is omitted in the diagram.

The image forming optical system 510 includes a first image forming optical system 510L and a second image forming optical system 510R. The first image forming optical system 510L and the second image forming optical system 510R are the same optical systems. The image forming optical system of the example 6 for example has been used for the two image forming optical systems.

An image pickup element 520L is disposed at an image position of the first image forming optical system 510L. An image pickup element 520R is disposed at an image position of the second image forming optical system 510R.

In both the first image forming optical system 510L and the second image forming optical system 510R, an image plane has a curved shape. The image pickup element 520L and the image pickup element 520R have a light-receiving surface (image pickup surface) having a curved shape, same as a shape of the image plane. By using the image pickup element 520L and the image pickup element 520R, it is possible to improve the quality of a photographic image.

The first image forming optical system 510L and the second image forming optical system 510R are disposed in parallel. Accordingly, in the image forming optical system 510, a pair of optical images having a parallax is formed. One of the optical images is picked up by the image pickup element 520L and the other optical image is picked up by the image pickup element 520R.

An image signal output from the image pickup element 520L and an image signal output from the image pickup element 520R are input to an image processing unit. In the image processing unit, a video signal for stereoscopic vision is generated. The video signal for stereoscopic vision is input to a display monitor for stereoscopic vision.

In the display monitor for stereoscopic vision, an image for a left eye and an image for a right eye are displayed alternately. By observing the two images with glasses for stereoscopic vision, the stereoscopic vision is possible.

According to the present embodiment, it is possible to provide an image pickup apparatus which includes an image forming optical system that is capable of forming a favorable image while being small-sized and having a long back focus.

In such manner, the present invention is suitable for an image pickup apparatus which includes an image forming optical system that is capable of forming a favorable image while being small-sized and having a long back focus.

What is claimed is:

1. An image pickup apparatus, comprising:
    an image forming optical system which includes an aperture stop that determines an axial light beam, and one cemented lens; and
    an image pickup element which is disposed on an image side of the image forming optical system, and which has a light-receiving surface that is not flat and is curved to be concave toward the image forming optical system,
    wherein:
        the cemented lens consists of, in order from an object side, a first lens having a negative refractive power, a second lens, and a third lens having a positive refractive power,
        the second lens is concave at an image side thereof, and there is no optical element with refractive power between the cemented lens and the image pickup element.

2. The image pickup apparatus according to claim 1, wherein the following conditional expression (1) is satisfied:

$$0.4 < |\Theta out60/60°| < 1.0 \qquad (1)$$

where:
    $\Theta out60$ denotes an angle made by a predetermined principal light ray emergent from an image-side surface of the third lens and an optical axis, and the predetermined principal light ray is a principal light ray for which an angle made with the optical axis is 60°, in a space on the object side of the first lens.

3. The image pickup apparatus according to claim 1, wherein the following conditional expressions (2) and (3) are satisfied:

$$0.7<|PS\times Rimg|<1.5 \quad (2), \text{ and}$$

$$0.7<|EXP/Rimg|<1.5 \quad (3)$$

where:
PS denotes Petzval's sum for the image forming optical system,
Petzval's sum PS is expressed by the following expression:

$$PS = \sum_{i=1}^{k} \frac{1}{n_i \times f_i},$$

i denotes an order of lenses from the object side in the image forming optical system,
k denotes a total number of lenses in the image forming optical system,
$n_i$ denotes a refractive index of an $i^{th}$ lens for a d-line,
$f_i$ denotes a focal length of the $i^{th}$ lens for the d-line,
EXP denotes a distance along an optical axis from the light-receiving surface to a paraxial exit pupil position of the image forming optical system, and has a negative sign when the paraxial exit pupil position is on the object side of the light-receiving surface, and
Rimg denotes a radius of curvature of a virtual spherical surface which includes a surface apex and a point in which a principal light ray incident at a maximum angle of view on the image forming optical system intersects the light-receiving surface, letting a point of intersection of the optical axis and the light-receiving surface be the surface apex.

4. The image pickup apparatus according to claim 1, wherein the aperture stop is disposed on one of a lens surface on the object side of the second lens, and a lens surface on the image side of the second lens.

5. The image pickup apparatus according to claim 1, wherein at least one of a cemented surface of the first lens and the second lens in the cemented lens, a cemented surface of the second lens and the third lens in the cemented lens, and an image-side surface of the third lens, is an aspherical surface.

6. The image pickup apparatus according to claim 1, wherein:
a lens surface on the image side of the first lens is a surface which is convex toward the object side, and
the following conditional expressions (4) and (5) are satisfied:

$$0\leq|R1R/R1L|<0.2 \quad (4), \text{ and}$$

$$0.25<R1R/f<0.5 \quad (5)$$

where:
R1R denotes a paraxial radius of curvature of the lens surface on the image side of the first lens,
R1L denotes a paraxial radius of curvature of a lens surface on the object side of the first lens, and f denotes a focal length for a d-line of the image forming optical system.

7. The image pickup apparatus according to claim 1, wherein the following conditional expression (6) is satisfied:

$$0\leq|SAGs1/TL|<0.05 \quad (6),$$

where:
SAGs1 denotes a distance in a direction along an optical axis from a surface apex of a lens surface on the object side of the first lens to a point at which a most peripheral effective light ray incident at a maximum image height on the image forming optical system passes through the lens surface on the object side of the first lens, letting a direction in which a light ray travels be a direction with a positive sign, and
TL denotes a distance on the optical axis from the lens surface on the object side of the first lens to the light-receiving surface.

8. The image pickup apparatus according to claim 1, wherein:
the second lens is a meniscus lens of which a convex surface is directed toward the object side, and
the following conditional expression (7) is satisfied:

$$0.02<THI2/TL<0.2 \quad (7),$$

where:
THI2 denotes a distance on an optical axis between surfaces of the second lens, and
TL denotes a distance on the optical axis from a lens surface on the object side of the first lens to the light-receiving surface.

9. The image pickup apparatus according to claim 1, wherein:
the third lens is a biconvex lens, and
the following conditional expression (8) is satisfied:

$$-1<(R3L+R3R)/(R3L-R3R)<0 \quad (8),$$

where:
R3L denotes a paraxial radius of curvature of a lens surface on the object side of the third lens, and
R3R denotes a paraxial radius of curvature of a lens surface on the image side of the third lens.

10. The image pickup apparatus according to claim 1, wherein the following conditional expression (9) is satisfied:

$$0.7<|\Theta out60/\Theta img60|<1.5 \quad (9),$$

where:
$\Theta out60$ denotes an angle made by a predetermined principal light ray emergent from an image-side surface of the third lens and an optical axis,
$\Theta img60$ denotes an angle made by a straight line connecting two predetermined points and the optical axis,
the predetermined principal light ray is a principal light ray for which an angle made with the optical axis is 60° in a space on the object side of the first lens, and
the two predetermined points are a point of intersection of the predetermined principal light ray emergent from the image-side surface of the third lens and the light-receiving surface, and a center of curvature of the light-receiving surface.

11. The image pickup apparatus according to claim 1, wherein the second lens is a resin lens.

\* \* \* \* \*